United States Patent
Yamanaka

(10) Patent No.: US 9,615,811 B2
(45) Date of Patent: Apr. 11, 2017

(54) RADIATION IMAGING APPARATUS AND METHOD FOR CONTROLLING THE SAME

(75) Inventor: Shinji Yamanaka, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 514 days.

(21) Appl. No.: 13/396,772

(22) Filed: Feb. 15, 2012

(65) Prior Publication Data

US 2012/0230469 A1 Sep. 13, 2012

(30) Foreign Application Priority Data

Mar. 7, 2011 (JP) ................................ 2011-049607

(51) Int. Cl.
*A61B 6/00* (2006.01)
(52) U.S. Cl.
CPC ............ *A61B 6/585* (2013.01); *A61B 6/5205* (2013.01); *A61B 6/5258* (2013.01)
(58) Field of Classification Search
CPC ...... A61B 6/5205; A61B 6/585; A61B 6/5258
USPC .................... 378/98.11, 98.12, 207
See application file for complete search history.

(56) References Cited

U.S. PATENT DOCUMENTS

| 2004/0256567 | A1 | 12/2004 | Nokita | 250/370.08 |
| 2010/0040199 | A1 | 2/2010 | Enomoto | 378/98.12 |
| 2012/0074328 | A1 | 3/2012 | Iijima | 250/370.08 |

FOREIGN PATENT DOCUMENTS

| CN | 1573533 | 2/2005 |
| EP | 2214399 | 8/2010 |
| JP | 11-136540 | 5/1999 |
| JP | 03190328 | 7/2001 |
| JP | 2006-158728 | 6/2006 |
| JP | 2010-172429 | 8/2010 |
| WO | 2010/004776 | 1/2010 |

OTHER PUBLICATIONS

English translation of JP 2006-158728, which was published on Jun. 22. 2006.*
Office Action issued on Mar. 17, 2014 in counterpart PRC patent application 201210058659.3, with translation.
Office Action issued on Jun. 26, 2015 in counterpart Japanese patent application 2011-049607, with English summary of pertinent portion.

* cited by examiner

*Primary Examiner* — Glen Kao
(74) *Attorney, Agent, or Firm* — Fitzpatrick, Cella, Harper & Scinto

(57) ABSTRACT

A radiation imaging apparatus performs radiation image obtaining processing in accordance with an exposure instruction, and obtains a radiation image. Then the radiation imaging apparatus performs offset correction for the obtained radiation image, and displays it. The radiation imaging apparatus determines, in accordance with a predetermined criterion, whether or not offset images obtained by offset image obtaining processing are stable over time. Then, if it is determined that the offset images are not stable, offset correction is performed by using an offset image obtained by performing offset image obtaining processing, following the obtaining of the radiation image. If it is determined that the offset images are stable, the offset correction is performed by using an offset image obtained before the obtaining of the radiation image.

20 Claims, 8 Drawing Sheets

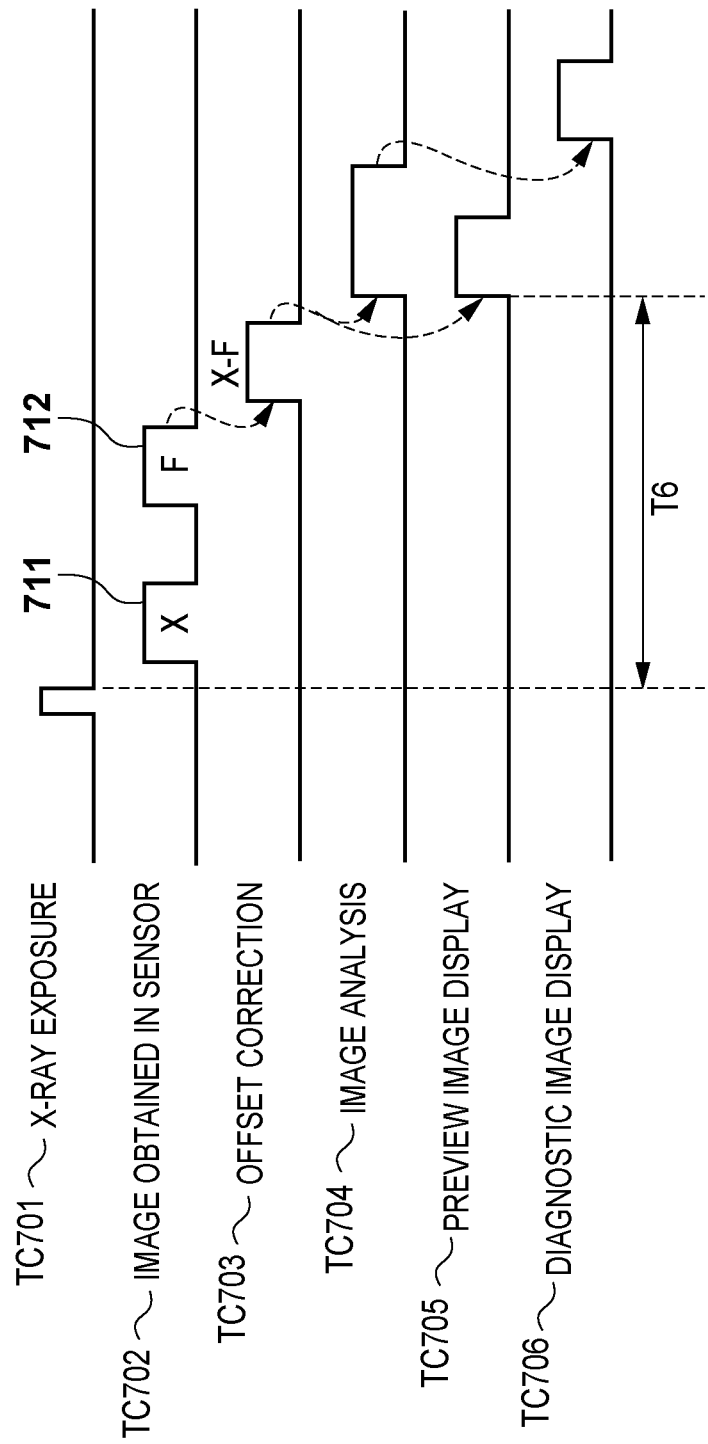

RADIATION IMAGING APPARATUS AND METHOD FOR CONTROLLING THE SAME

BACKGROUND OF THE INVENTION

Field of the Invention

The present invention relates to a radiation imaging apparatus and a method for controlling the same.

Description of the Related Art

Currently, in X-ray still image imaging systems in medicine, film methods are common in which X-rays are irradiated onto an object to be imaged, and the transmitted X-ray image is exposed on a film. Film methods offer the functionality of displaying and recording information, they permit for a large area, are excellent in gradation characteristics, and in addition, are light weight and easy to handle. Thus, film methods are widespread throughout the world. However, film methods require space, man-power and time, due to the complication of requiring a development process, as well as for long-term storage and accessibility.

Recently, the demand for digital X-ray images has been increasing in hospitals. Radiation imaging apparatuses that, instead of films, convert radiation into electric signals by a plurality of radiation detection elements arrayed in a two-dimensional matrix and form an image have been put to use. In these types of radiation imaging apparatuses, an X-ray detector (FPD: Flat Panel Detector) in which solid-state imaging elements are arrayed in a two-dimensional matrix, and which converts an X-ray dose into an electric signal is used. With X-ray imaging apparatuses having such an X-ray detector, since it is possible to convert an X-ray image into digital information, it is possible to transmit image information to a remote location, and, what is more, instantaneously. By transmitting information of an X-ray image, there is the advantage that it is possible to receive an advanced diagnosis equal to that of a university hospital in a city center while in a remote location. In addition, films are not used, and thereby, there is the advantage that storage space required for films in hospitals is reduced. In the future, with the introduction of superior image processing techniques, the realization of automated diagnoses in which a diagnosis is made using a computer without a radiologist is expected.

X-ray detectors such as FPDs (hereinafter, referred to as sensors) include a photoelectric conversion circuit in which a plurality of photoelectric conversion elements that convert radiation into an electric signal are arrayed in a matrix, and a read-out circuit for reading out, from this photoelectric conversion circuit, the electric signal obtained by this conversion. When X-rays are irradiated onto an object to be imaged, the photoelectric conversion according to the transmitted X-rays is performed by photoelectric conversion elements of a photoelectric conversion circuit, and the signal charges corresponding to the transmitted X-ray doses are accumulated in the photoelectric elements. A read-out circuit drives the signal lines of the photoelectric conversion circuit, and controls, as appropriate, switching elements to which the photoelectric conversion elements are connected. Thereby the read-out circuit successively reads out the signal charges accumulated in the photoelectric conversion elements as electric signals, amplifies them, and outputs them.

By the operation as described above, it is possible to read an image of the person to be imaged with the electric signals output from the read-out circuit. However, an offset generated in the photoelectric conversion circuit and the read-out circuit is included in the image thus read-out (the electric signals output from the read-out circuit, representing the image). Causes of the offset may be: (A) dark currents in the photoelectric conversion elements, (B) leak currents in the switching elements, (C) offset voltages in the amplifiers of the read-out circuit, and the like.

Since images obtained by irradiating X-rays include offsets as described above, the offset components must be removed. The processing for removing such an offset component is referred to as offset correction. The processing of ordinary offset correction will now be described. FIG. 7 is a diagram showing a timing chart of ordinary offset correction. When a still image is imaged, if an X-ray exposure is performed at the timing shown in chart TC701 by an exposure instruction of an operator, the X-ray imaging apparatus drives a sensor at the timing shown in chart TC702, and obtains an X-ray image (X) (at timing 711 in FIG. 7). Subsequently, the X-ray imaging apparatus drives the sensor in a state in which no X-rays are irradiated, and obtains an offset image (F) (timing 712 in FIG. 7). The X-ray imaging apparatus subtracts the above-described offset image (F) from the above-described X-ray image (X) at the timing shown in chart TC703 (X-F), and displays a preview image for the operator to determine the success/failure of the imaging, at the timing shown in chart TC705. Furthermore, the X-ray imaging apparatus performs an image analysis for using the image (X-F) in an actual diagnosis, at the timing shown in chart TC704, by using the image (X-F) in which offset correction is performed. When this is finished, a diagnostic image is displayed at the timing shown in a chart TC706.

However, in the above-described offset correction method, since the offset image is obtained after X-ray irradiation (timing 712), there is a problem in that the time period (T6 in FIG. 7) from the X-ray irradiation to the display of a preview image becomes longer. In order to shorten the time period from X-ray irradiation to the display of a preview image, a method for obtaining an offset image before X-ray irradiation, the imaging by a video camera or the like is described in Japanese Patent No. 03190328 (hereinafter, Document 1). In the method described in Document 1, offset images are periodically obtained, and the offset image obtained at the timing closest to imaging is used for the actual correction.

However, if offset images are periodically obtained as in Document 1, when the timing for obtaining an offset image and the instruction of an X-ray exposure overlap, the X-ray exposure is performed after obtaining the offset image. That is, there are cases where variations occur in the time periods from the instruction of an X-ray exposure to the X-ray exposure, and the instantaneousness of the X-ray exposure instructions is compromised. In addition, in the analysis of an X-ray image, although it is preferable to use the offset image immediately after the X-ray image is obtained, an offset image before an X-ray image is obtained is used in the technique in Document 1. Therefore, it is difficult to assure the accuracy of the offset correction. Particularly, high-accuracy offset correction is difficult at or near the startup of an apparatus in which the amount of offset fluctuates.

SUMMARY OF THE INVENTION

The present invention is made in view of the above-described problems. According to a preferred embodiment thereof, there is provided a radiation imaging apparatus, and a method for controlling the same in which, while the accuracy of offset correction is maintained, it is possible to shorten the time from a radiation exposure to an image display.

According to one aspect of the present invention, there is provided a radiation imaging apparatus comprising: a sensor that obtains radiation that has been transmitted through an object to be imaged as a radiation image; and a processing unit configured to perform offset correction processing on the radiation image using either an offset image obtained with the sensor after obtaining the radiation image, or an offset image obtained with the sensor before obtaining the radiation image, depending on an evaluation value of the offset images.

Also, according to another aspect of the present invention, there is provided a method for controlling a radiation imaging apparatus comprising the steps of: obtaining radiation that is transmitted through an object to be imaged as a radiation image; and performing offset correction processing on the radiation image using either an offset image obtained after obtaining the radiation image or an offset image obtained before obtaining the radiation image, depending on an evaluation value of offset images obtained in the obtaining step.

Further features of the present invention will become apparent from the following description of exemplary embodiments with reference to the attached drawings.

BRIEF DESCRIPTION OF THE DRAWINGS

FIG. 7 is a timing chart of offset correction by an ordinary X-ray imaging apparatus.

DESCRIPTION OF THE EMBODIMENTS

Figure 1:
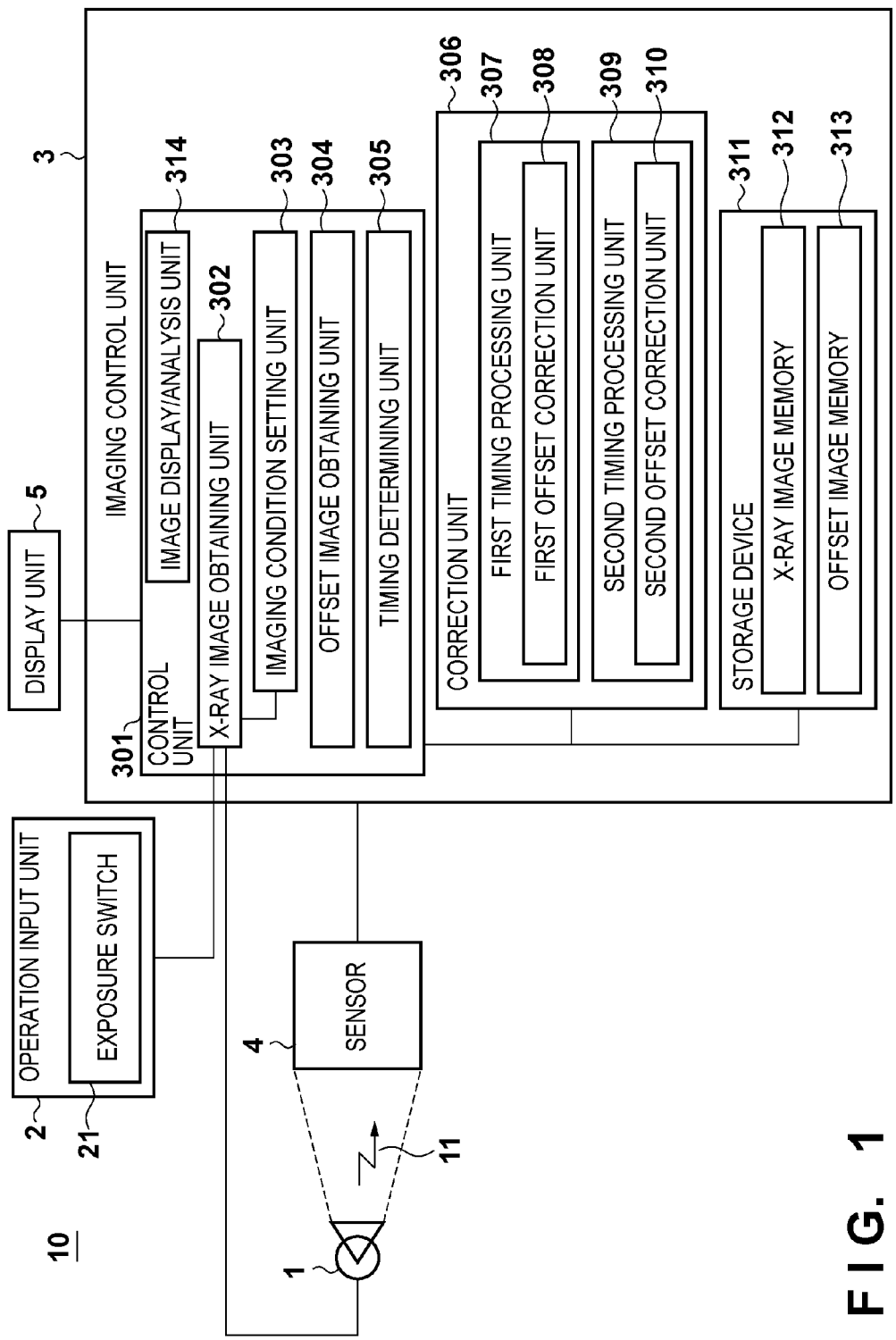
FIG. 1 is a block diagram showing a configuration example of an X-ray imaging apparatus according to an embodiment.

One example of a preferred embodiment of the present invention will now be described with reference to the accompanying drawings. In the following embodiments, an X-ray imaging apparatus will be described as an example of a radiation imaging apparatus that obtains an X-ray image as a radiation image by imaging using X-rays as radiation. FIG. 1 is a block diagram showing one example of a schematic configuration of an X-ray imaging apparatus according to the present embodiment.

As shown in FIG. 1, an X-ray imaging apparatus 10 according to the present embodiment includes an X-ray generating unit 1, an operation input unit 2, an imaging control unit 3, a sensor 4, and a display unit 5. The imaging control unit 3 includes a control unit 301, a correction unit 306, and a storage device 311. The control unit 301 includes a CPU (not shown), and functions as an X-ray image obtaining unit 302 serving as a radiation image obtaining processing unit, an imaging condition setting unit 303, an offset image obtaining unit 304, a timing determining unit 305, and an image display/analysis unit 314. In addition, the correction unit 306 functions as a first timing processing unit 307 having a first offset correction unit 308 and a second timing processing unit 309 having a second offset correction unit 310. The correction unit 306 may be configured by a field programmable gate array (FPGA) or the like, and may be realized by the CPU of the control unit 301 or a CPU separate from that of the control unit 301. In addition, the storage device 311 includes an X-ray image memory 312 for storing an X-ray image obtained by the X-ray image obtaining unit 302, and an offset image memory 313 for storing an offset image obtained by the offset image obtaining unit 304.

The X-ray generating unit 1 serving as a radiation generating unit can generate X-rays 11 for an object to be imaged (person to be examined), and includes, for example, an X-ray tube. The operation input unit 2 is operated when a user inputs an instruction into the X-ray imaging apparatus. The operation input unit 2 includes an exposure switch 21 for the user to instruct the X-ray generating unit 1 to generate the X-rays 11. In addition, instructions for setting imaging conditions may be allowed via the operation input unit 2.

The X-ray image obtaining unit 302 performs X-ray imaging processing, by letting the X-ray generating unit 1 irradiate the X-rays 11 during the accumulation of electric charges in the sensor 4, and thereafter, performing the read-out of the electric charges from the sensor 4. The X-ray image thus obtained is stored in the X-ray image memory 312. The offset image obtaining unit 304 performs imaging processing of an offset image, by performing the accumulation of electric charges in the sensor 4 in the state (non-irradiation state) in which the X-ray generating unit 1 does not irradiate the X-rays 11, and thereafter, performing the read-out of the electric charges from the sensor 4. The offset image thus obtained is stored in the offset image memory 313.

The timing determining unit 305 references a predetermined number of offset images, stored in the offset image memory 313, and determines, from the change over time of the offset images, whether or not the change amount is at least a predetermined threshold. Then, the timing determining unit 305 switches the timing of obtaining offset images based on this determination. The timing determining unit 305 determines whether to use the first timing processing unit 307 that uses a first offset image obtaining timing or the second timing processing unit 309 that uses a second offset image obtaining timing. Thus, the timing determining unit 305 switches, based on the extent of the stability of offset images, the timing of obtaining offset images, and in addition, switches the offset image obtained at the respective timing that is used, in the correction for a preview display. The details of the operation of the first timing processing unit 307 and the second timing processing unit 309 will be described further below. Also, the first offset correction unit 308 performs offset correction using an offset image that the first timing processing unit 307 has obtained using the offset image obtaining unit 304. In addition, the second offset correction unit 310 performs offset correction by using an offset image that the second timing processing unit 309 obtains by using the offset image obtaining unit 304. The image display/analysis unit 314 performs the analysis processing of X-ray images and the display control of preview images displayed on the display unit 5.

The sensor 4 detects, as an electric signal (electric charge), the X-rays 11 that are irradiated from the X-ray generating unit 1 and transmitted through the person to be imaged, under control of the X-ray image obtaining unit 302 in the imaging control unit 3. In addition, the sensor 4 detects an electric signal (electric charge) in the state in which no X-rays 11 are irradiated from the X-ray generating unit 1, i.e., in an offset state, under control of the offset image obtaining unit 304 in the imaging control unit 3.

In the sensor 4, pixels including a photoelectric conversion element and a TFT, for example are arranged in a two-dimensional array. A fluorescent substance, for example, is provided and formed on the pixels. The X-rays entering the sensor 4 are converted into visible light by the fluorescent substance. The converted visible light enters the photoelectric conversion elements of the pixels. Thus, electric charges corresponding to the visible light are generated in the photoelectric conversion elements. Also, in the present embodiment, "conversion elements" are provided that convert incident X-rays into electric charges with a fluorescent substance and photoelectric conversion elements. However, a configuration is also possible in which no fluorescent substance is provided and so-called direct conversion type conversion elements that convert incident X-rays directly into electric charges are used. Therefore, in the following description, the description will be given on the assumption that "conversion elements" are two-dimensionally arrayed in the sensor 4. In addition, as already described in the section titled "Description of the Related Art", the sensor 4 alternately repeats the accumulation of electric charges of the conversion elements and the read-out of the electric charges, and thereby can image an X-ray image and an offset image.

The display unit 5 displays an X-ray image based on the electric charges read out from the sensor 4, an operation UI, and the like, based on the control of the imaging control unit 3. The imaging condition setting unit 303 may let the display unit 5 display the operation UI, and let a user enter an instruction for setting various imaging conditions.

When the exposure switch 21 is turned on by the operation of a user, the imaging control unit 3 controls the X-ray generating unit 1 so that it irradiates the X-rays 11. In addition, the imaging control unit 3 reads out the electric charges based on the X-rays 11 transmitted through an object to be imaged (person to be examined) from the sensor 4 in synchronization with the irradiation of the X-rays 11, and generates an X-ray image. Then the imaging control unit 3, after performing the image processing including offset correction processing, displays the X-ray image on the display unit 5.

Figure 2:
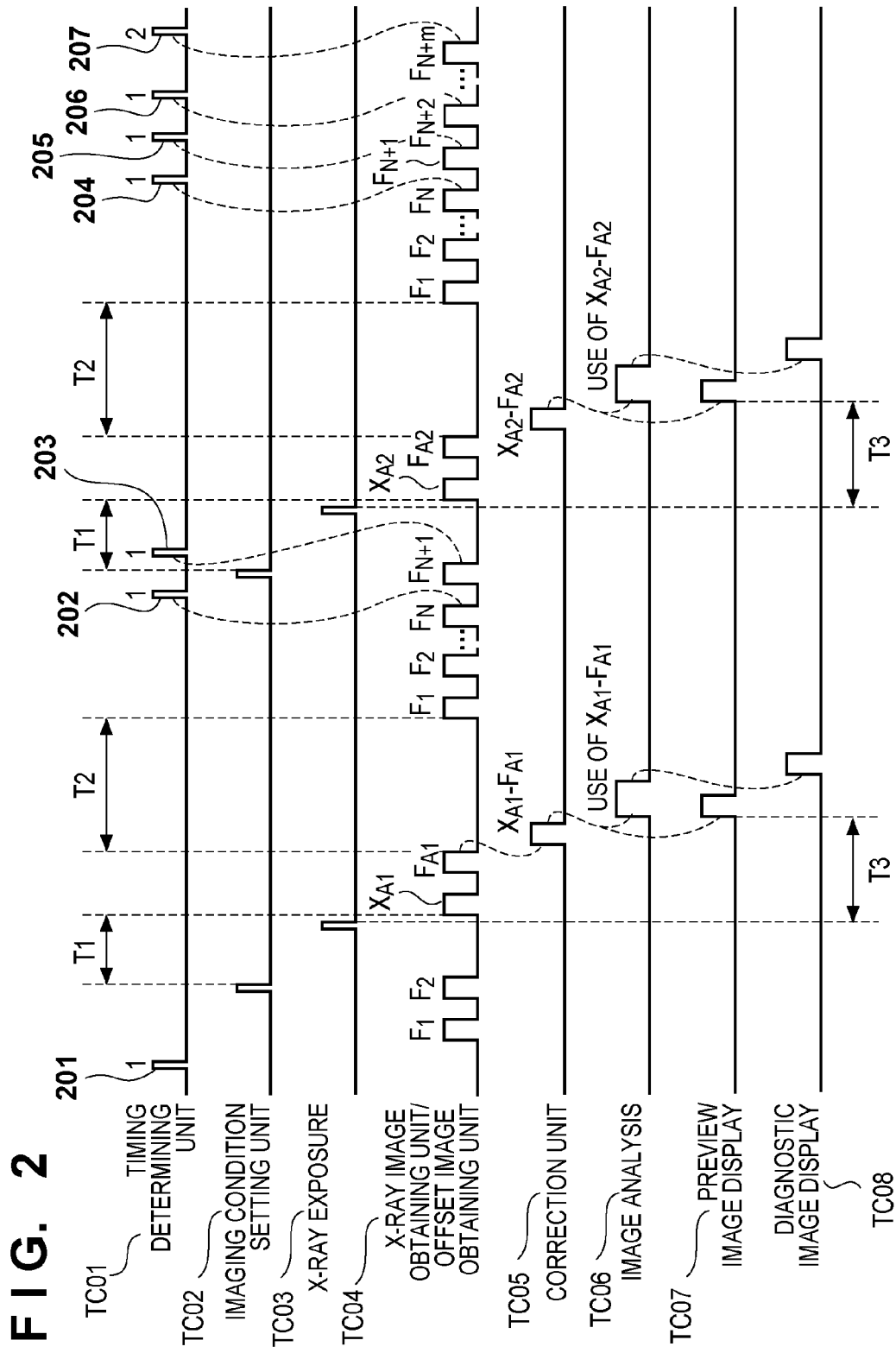
FIG. 2 is a timing chart of a process for obtaining a first offset image.
Figure 3:
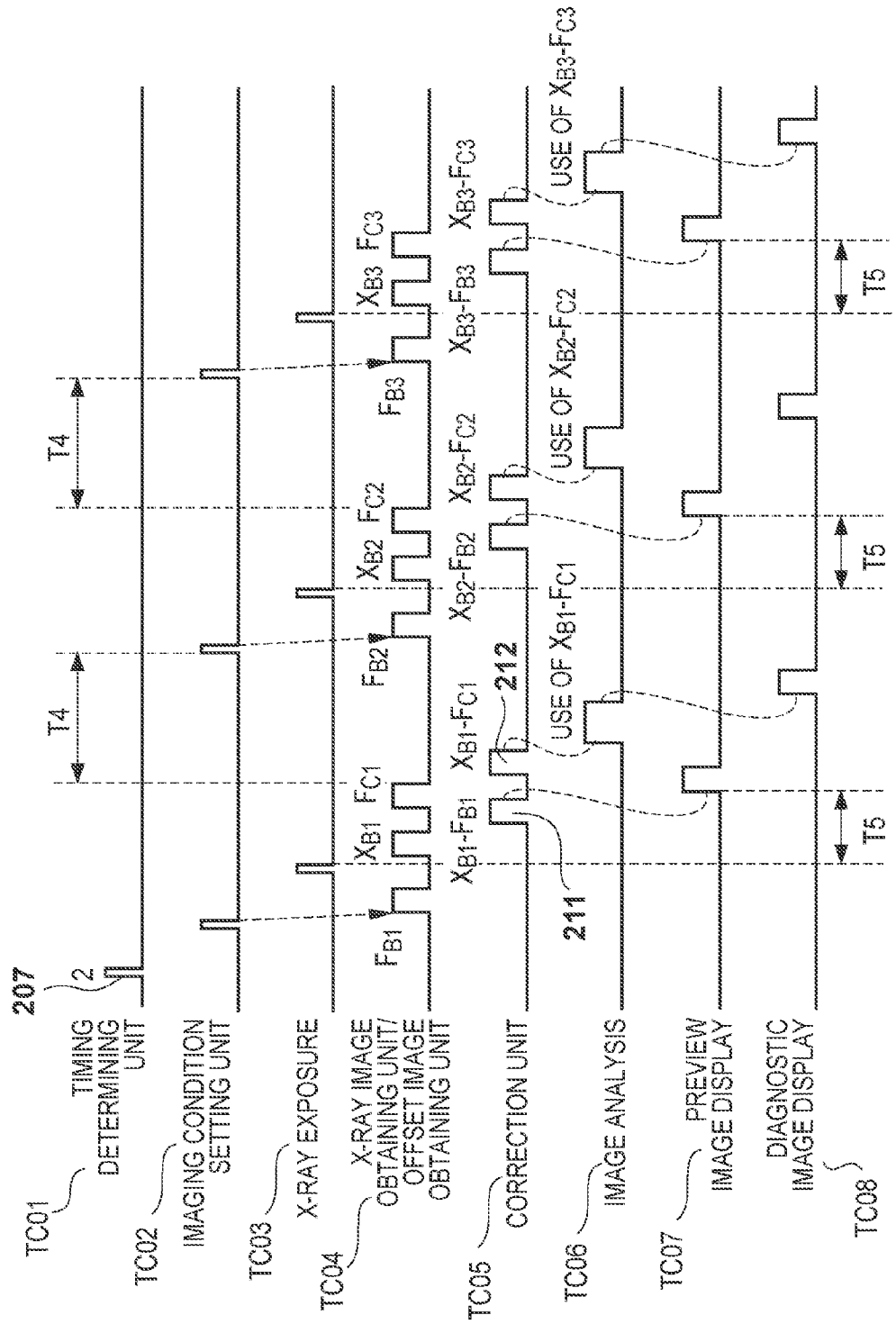
FIG. 3 is a timing chart of a process for obtaining a second offset image.

FIG. 2 is a timing chart showing the X-ray imaging operation of the case where the first timing processing unit 307 is selected. FIG. 3 is a timing chart showing the X-ray imaging operation of the case where the second timing processing unit 309 is selected. The details of the operation shown in FIGS. 2 and 3 will be described below with reference to the flow charts of FIGS. 4 through 6. First, the operation of the units shown in FIG. 1 will be described with reference to the timing charts shown in FIGS. 2 and 3.

In FIGS. 2 and 3, chart TC01 shows signals of the timing determining unit 305. "1" in the chart TC01 denotes that a first offset image obtaining timing is selected, and "2" in the chart TC01 denotes that a second offset image obtaining timing is selected. The timing determining unit 305 selects the first offset image obtaining timing at the startup of the apparatus (timing 201). Then, if the offset images of at least a predetermined number of offset images (at least N, namely the images $F_1$ to $F_N$ in the present embodiment) are stored in the offset image memory 313, the change amount among the offset images is calculated, and the timing to be used is determined (timings 202 to 207). If the change amount among the offset images is less than a predetermined threshold, it is determined that the offset images are stable, and the timing determining unit 305 selects the second offset image obtaining timing (timing 207). Therefore, the operation of the first offset image obtaining timing is indicated before timing 207 (FIG. 2) of the timing chart, and the operation of the second offset image obtaining timing is indicated after timing 207 (FIG. 3) in the timing chart.

Chart TC02 shows signals indicating that a user sets imaging conditions such as an X-ray tube voltage and an X-ray tube current, with the operation UI of the display unit 5 or the like. These signals are output by the imaging condition setting unit 303. Chart TC03 shows timings at which the X-ray image obtaining unit 302 lets the X-ray generating unit 1 perform X-ray exposures in accordance with the operation of the exposure switch 21. Chart TC04 shows the operation by which the X-ray image obtaining unit 302 or the offset image obtaining unit 304 obtains images from the sensor 4. Here, $F_x$ (for any x) denotes the timings at which the offset image obtaining unit 304 obtains offset images. $X_y$ (for any y) denotes the timings at which the X-ray image obtaining unit 302 obtains X-ray images.

Chart TC05 shows timings at which the first offset correction unit 308 or the second offset correction unit 310 performs offset correction. The operation timing of the first offset correction unit 308 is shown during the period when operation is performed at the first offset image obtaining timing. The operation timing of the second offset correction unit 310 is shown during the period when operation is performed at the second offset image obtaining timing. Chart TC06 shows periods during which the image display/analysis unit 314 performs image analyses for the images in which offset correction is finished, and the processing to allow an operator to use them in a diagnosis. Chart TC07 shows timings for displaying preview images on the display unit 5 by the image display/analysis unit 314. Preview images are the simplified displays for an operator to determine the success or failure of imaging. In addition, a preview image can be immediately displayed, if the offset correction of the chart TC05 is finished. Chart TC08 shows timings at which the image display/analysis unit 314 outputs, to the display unit 5, diagnostic images that an operator uses in an actual diagnosis. The display of a diagnostic image cannot be performed, until an image analysis shown in the chart TC06 is finished.

As shown in the timing chart of FIG. 2, the first offset correction unit 308 operating during the first offset image obtaining timing period performs correction by using the offset image that the offset image obtaining unit 304 obtains immediately after X-ray imaging. That is, the first offset correction unit 308 performs the correction for a preview image and the correction for generating a diagnostic image by using the offset image obtained following the X-ray imaging. In contrast, the second offset correction unit 310 operating during the second offset image obtaining timing period uses the offset images obtained before and after X-ray imaging, as shown in the timing chart (timings 211 and 212) of FIG. 3. The second offset correction unit 310 corrects an X-ray image by using the offset image obtained before the X-ray imaging, and generates a preview image for preview display (timing 211). Therefore, the display of a preview image can be rapidly preformed. Then, the second offset correction unit 310 corrects the X-ray image by using the offset image obtained following the X-ray imaging, and uses it for the generation of a diagnostic image (timing 212).

Figure 4:
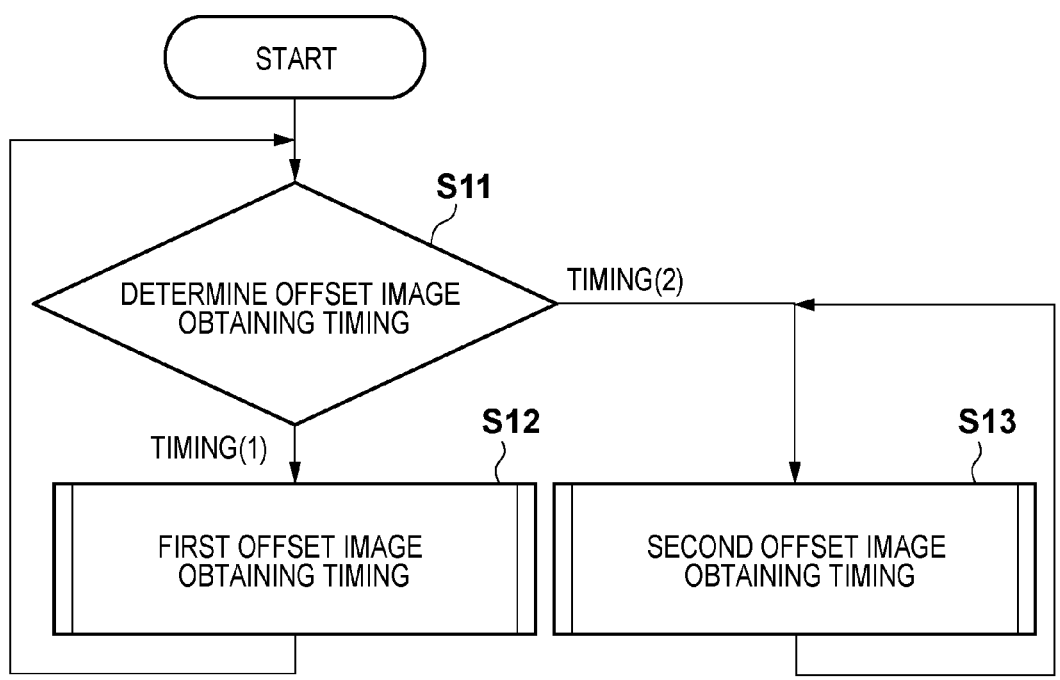
FIG. 4 is a flow chart showing processing of an X-ray imaging apparatus according to an embodiment.
Figure 5A:
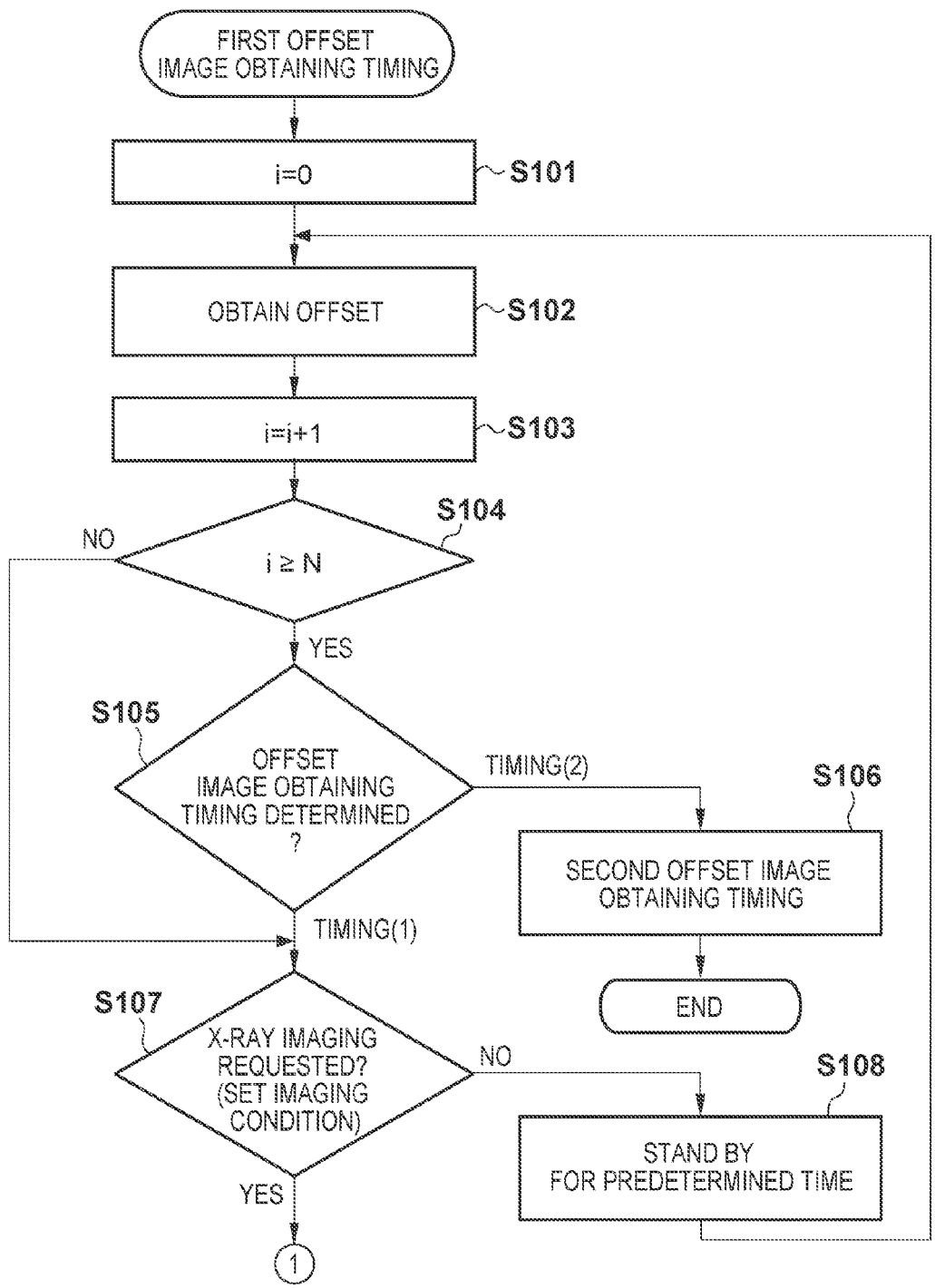
FIGS. 5A and 5B are flow charts showing the first offset image obtaining processing.
Figure 5B:
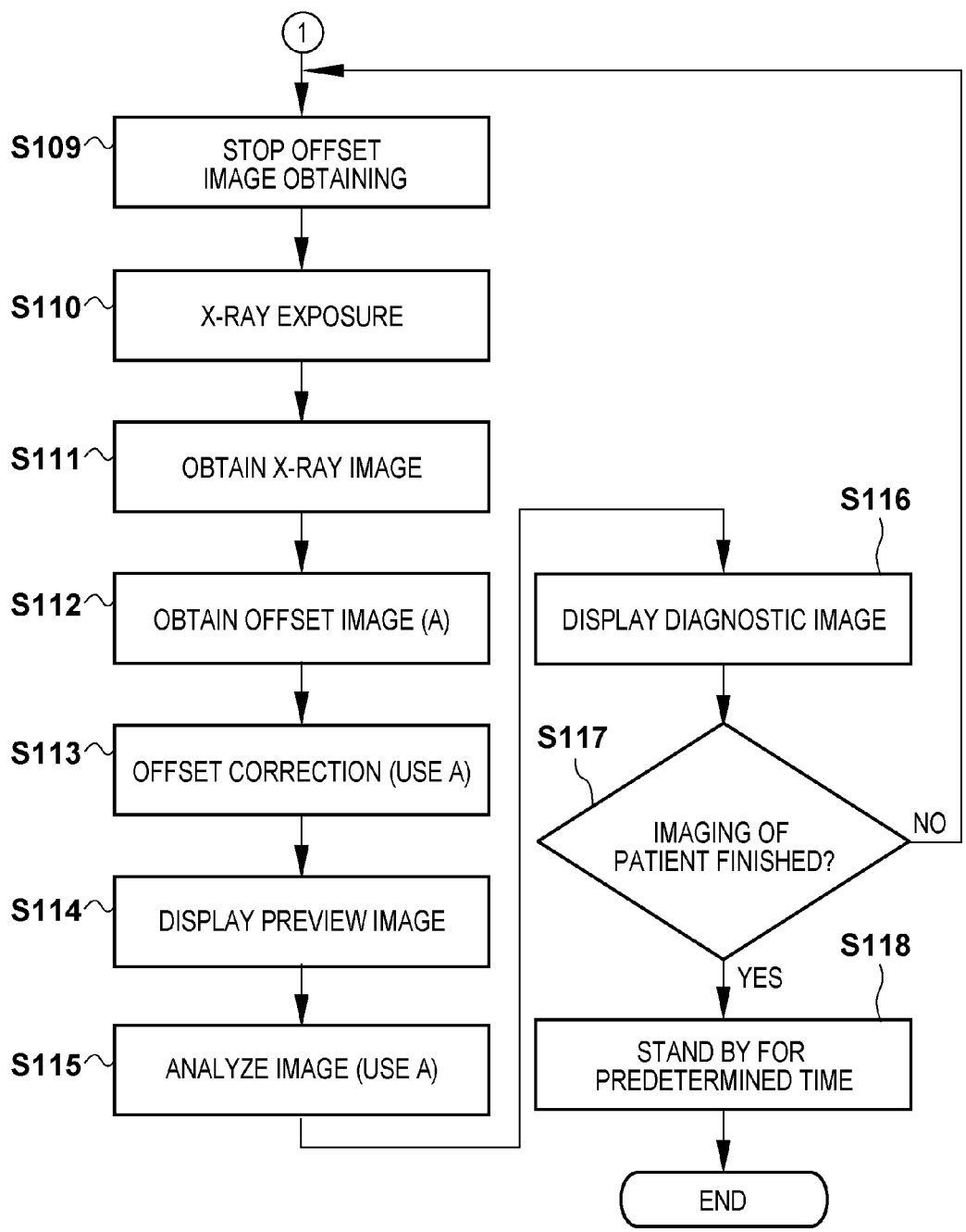
Figure 6:
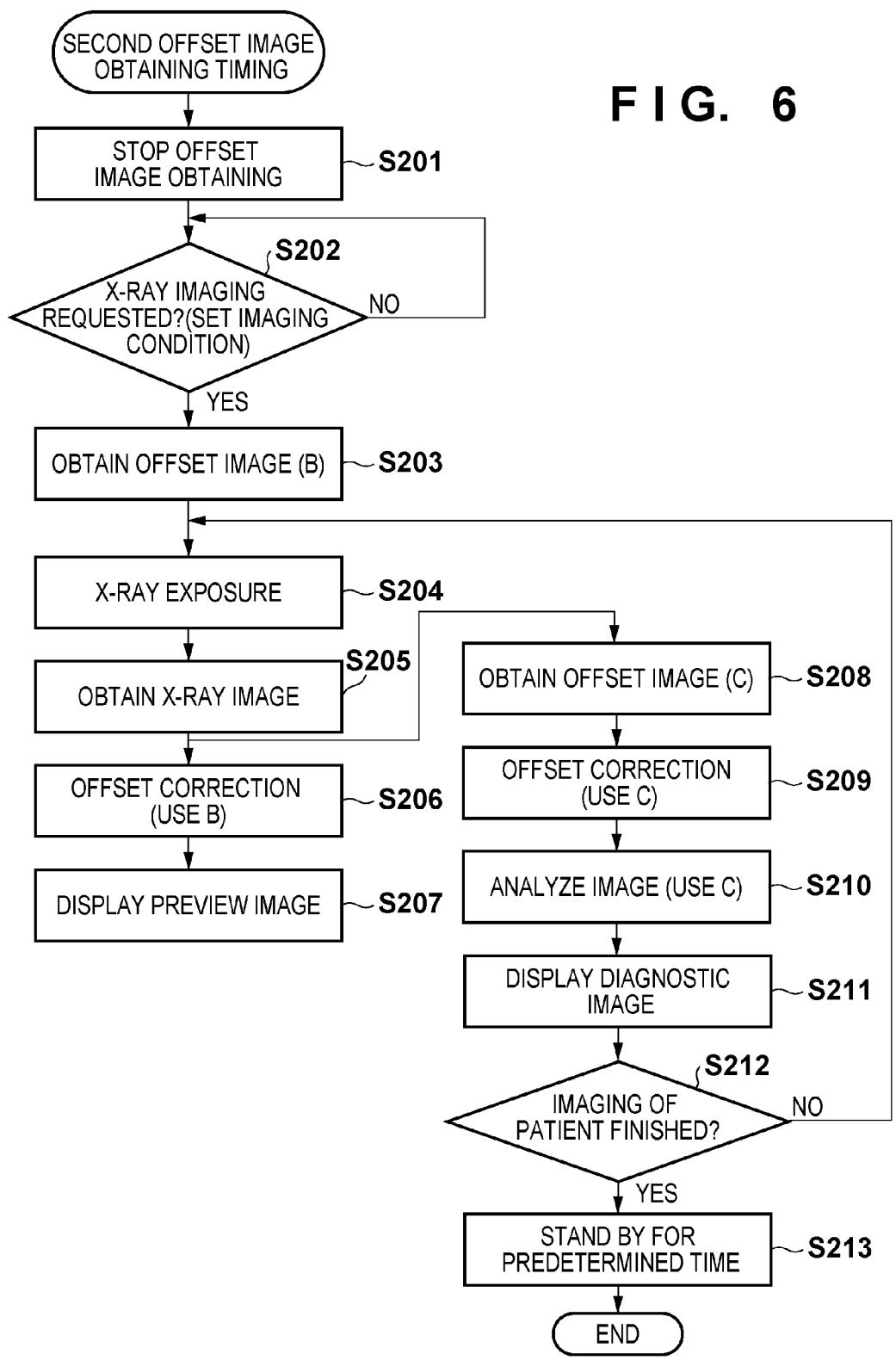
FIG. 6 is a flow chart showing the second offset image obtaining processing.

FIGS. 4 through 6 are flow charts showing the operation of an X-ray imaging apparatus according to the present embodiment. The operation of the X-ray imaging apparatus according to the present embodiment will now be described based on these flow charts and the timing charts of FIGS. 2 and 3. Also, the constant N in the flow chart of FIGS. 5A and 5B is the predetermined number of the offset images that need to be obtained in order for the timing determining unit 305 to determine the timings of obtaining offset images from the change over time of the offset images. In addition, the variable i is the number of the offset images actually obtained.

In FIG. 4, in step S11, the timing determining unit 305 determines whether the first offset image obtaining timing (timing (1)) or the second offset image obtaining timing (timing (2)) is used. Here, the obtaining of offset images is performed by the first timing processing unit 307, in timing (1), and obtaining processing is performed by the second timing processing unit 309, in timing (2). At the start of operation such as at power up and the like, timing (1) is selected, and timing (1) is maintained until timing (2) is selected in S105 described below. If it is determined that timing (1) is selected in step S11, the processing (FIGS. 5A and 5B) with the first offset image obtaining timing as shown in FIG. 2 is performed by the first timing processing unit 307 in step S12. If it is determined that timing (2) is selected in step S11, the processing (FIG. 6) with the second offset image obtaining timing as shown in FIG. 3 is performed by the second timing processing unit 309 in step S13. After the second offset image obtaining timing is selected, the processing by the second offset image obtaining timing continues (S13).

FIGS. 5A and 5B are a flow chart showing the processing by the first offset image obtaining. First, in step S101, the timing determining unit 305 sets the number of obtained offset images (variable i) to 0. In step S102, the first timing processing unit 307 obtains an offset image by using the offset image obtaining unit 304, and stores it in the offset image memory 313. In step S103, the number of obtained offset images (variable i) is incremented by one. In step S104, the timing determining unit 305 determines whether a predetermined number (N) of offset images have been obtained (stored in the offset image memory 313). If a predetermined number of offset images have been obtained (i≥N), the timing determining unit 305 detects, from N offset images stored in the offset image memory 313, their change over time, in step S105. The timing determining unit 305 determines the stability of offset images over time, based on the change over time of the offset images. If it is determined that the offset images are stable, then processing is switched so that operation is performed with timing (2). That is, in step S106, the second offset image obtaining timing is selected, and the processing ends. After this, the processing proceeds from step S11 to step S13, and the processing (FIG. 6) by the second timing processing unit 309 is performed.

Also, the fact that offset images are stable means that the change amount of the obtained offset images is strictly less than a predetermined threshold. However, in mounting onto the apparatus, determining whether or not offset images is stable over time may be performed based on a predetermined criterion, for example, when determining that the mean value of the obtained offset images is less than a predetermined threshold when determining that the difference between the previous offset mean value and the present offset value is not more than a predetermined threshold, when determining that a predetermined time period simply passes from sensor drive start (power up of the sensor), and the like. In addition, as the offset images that the timing determining unit 305 uses for determination, the latest N offset images may always be used, or all of the at least N stored offset images may be used.

If it is determined that the predetermined number (N) of offset images has not been obtained in step S104 or timing (1) is selected in step S105, the processing proceeds to step S107. In step S107, if there is no X-ray imaging request (condition setting request) from the imaging condition setting unit 303, after the first timing processing unit 307 stands by for a given time in step S108, the processing returns to S102. Thus, until the timing determining unit 305 selects timing (2) or an X-ray imaging request is issued from the imaging condition setting unit 303, the first timing processing unit 307 obtains offset images at a constant time interval. Thus, if N offset images are stored in the offset image memory 313, the determination of switching of timing by the timing determining unit 305 is performed.

In step S107, if there is an X-ray imaging request, the first timing processing unit 307 first stops the obtaining of offset images described above in step S109. Subsequently, in step S110, the X-ray image obtaining unit 302 lets the X-ray generating unit 1 perform an X-ray exposure in response to the user operation of the exposure switch 21, and in step S111, the X-ray image obtaining unit 302 obtains the X-ray image from the sensor 4. After the X-ray image has been obtained, the first timing processing unit 307 obtains an offset image with the offset image obtaining unit 304, in step S112. In step S113, the first offset correction unit 308 performs offset correction on the X-ray image obtained in step S111, using the offset image obtained in step S112. In step S114, the image display/analysis unit 314 displays the image that has been subjected to offset correction in step S113, as a preview image, on the display unit 5. In step S115, while the preview image is displayed, the image display/analysis unit 314 performs an image analysis on the image corrected in step S113 in order to generate an image to be used for diagnosis. Then, in step S116, the image display/analysis unit 314 generates a diagnostic image, and displays it on the display unit 5.

Subsequently, in step S117, the first timing processing unit 307 determines whether or not the imaging of the same patient is continued. This determination can be performed based on whether the imaging condition has been reset or not (whether the patient's name has been reset or not), for example. If the imaging of the same patient is continued, the processing returns to step S109, and the above-described processing is repeated. In addition, if it is determined that the imaging of the patient is finished (this determination can be performed based on an explicit user operation indicating the imaging end, for example), the processing advances to step S118. In step S118, in order to prevent the afterimage due to the X-ray imaging from exerting an effect on the offset images for offset image obtaining timing determination, the first timing processing unit 307 stops the obtaining of offset images for the period T2 in FIG. 2. Subsequently, when the processing is ended, the processing returns to S11 (FIG. 4). Since timing (1) is maintained, the processing of FIGS. 5A and 5B, i.e., the processing from step S101 is started again.

With the above operation, the time period from the X-ray exposure to the display of the image on the display unit 5 of FIG. 1 is T3 in FIG. 2. In the above operation of the first offset image obtaining timing, the offset image obtaining processing for obtaining the offset image used in the correction of an X-ray image is not performed before an X-ray exposure (X-ray image obtaining processing). This is because there may be a possibility that the X-ray image cannot be accurately corrected due to instability of the offset images with the offset image imaged prior to an X-ray exposure allows. In the present embodiment, the time period between the X-ray image obtaining processing in step S111 and the offset image obtaining processing in step S112, in FIG. 5B is extremely short. Therefore, it is assumed that there is no large difference between the pixel values of an offset image at the time of step S111 and the pixel value of an offset image at the time of step S112. In this manner, while offset images are not stable, a highly accurate correction is realized by performing an offset correction method with the first offset image obtaining timing.

FIG. 6 shows a flow chart of the second offset image obtaining timing. In step S105 of FIG. 5A, if it is determined that the change over time of the offset images is small (the offset images are stable), a transition to the second offset image obtaining timing is performed. In the operation by the second offset image obtaining timing, since the timing determining unit 305 stops its processing, it is not necessary to obtain the offset images for obtaining the change over time of offset images. Therefore, first, the second timing processing unit 309 stops the obtaining of offset images, in step S201. Then, in step S202, the second timing processing unit 309 waits for an X-ray imaging request (setting imaging condition) from the imaging condition setting unit 303. In step S202, if it is determined that there is an X-ray imaging request, the second timing processing unit 309 lets the offset image obtaining unit 304 obtain an offset image prior to an X-ray exposure in step S203. Subsequently, in step S204, the X-ray image obtaining unit 302 lets the X-ray generating unit 1 generate the X-rays 11 and performs an X-ray exposure in accordance with a signal (exposure instruction) from the exposure switch 21. In step S205, the X-ray image obtaining unit 302 obtains an X-ray image. When the X-ray image has been obtained, in step S206, the second offset correction unit 310 performs the offset correction of the X-ray image obtained in step S205 using the offset image obtained in step S203 (timing 211). In step S207, the image display/analysis unit 314 performs a preview display for determining the success/failure of imaging, on the display unit 5, using the image subjected to offset correction in step S206. Also, the offset image obtained in step S203 is used for the image generation for preview display, but not for the generation of a diagnostic image.

While a preview image is displayed in step S207, the second timing processing unit 309 obtains an offset image for generating a diagnostic image using the offset image obtaining unit 304, in step S208. Then, in step S209, the second offset correction unit 310 performs the offset correction on the X-ray image obtained in step S205 using the offset image obtained in step S208 (timing 212). In step S210, the image display/analysis unit 314 performs an image analysis on the image subjected to offset correction in step S209, and generates a diagnostic image. Then, in step S211, the image display/analysis unit 314 displays it on the display unit 5. In step S212, the second timing processing unit 309 determines whether the imaging of the same patient is finished, in a manner similar to step S117. If it is not finished, the processing returns to step S204, and the above-described processing is repeated. If the imaging of the same patient is continued, the offset image obtained in S203 is reused in the offset correction of step S206. That is, the offset image used in step S206 is the offset image obtained in step S203, of the initial imaging of the patient. In addition, if the imaging of the patient is finished, the obtaining of offset images is stopped for the time period T4 in FIG. 3, in step S213, in order to prevent the afterimage due to the X-ray imaging from exerting an effect on the offset image. Then, the processing shown in FIG. 6 is repeated.

Also, in the above-described processing, when a plurality of exposure instructions is repeated after a single instruction for setting imaging conditions, the offset image that the offset image obtaining unit 304 obtains in response to the input of this single setting instruction is used for the offset correction for preview images (S206). However, the present invention is not limited to this, and the latest obtained offsets image may always be used in step S206. In this case, in step S206 at the second and subsequent times, not the offset image obtained in step S203 but the offset images obtained in step S208 may be used.

By the above operation, in the second offset image obtaining timing, the time period from an X-ray exposure to the display of a preview image on the display unit 5 is T5 in FIG. 3. In the operation in the second offset image obtaining timing, the time to preview display is shortened by using the offset image obtained before the X-ray imaging obtaining processing, in order to generate a preview image. This is because, due to the operation of the case where it is determined that the change over time of the pixel values of offset images is not more than a predetermined value as described above, even if the offset image obtained prior to an X-ray exposure is used in offset correction, a highly accurate correction can be performed.

There is no difference in terms of the preview image display after an X-ray exposure, in step S114 of FIG. 5B and step S207 of FIG. 6. However, in step S207, an offset correction image is obtained before the X-ray exposure and X-ray image obtaining of step S204 and step S205 (step S203). Therefore, T5 in FIG. 3 can be made shorter than T3 in FIG. 2, since the offset correction processing of step S206 can be performed from immediately after the X-ray image obtaining of step S205. Thus, there is a feature that the display following an X-ray exposure is fast.

As described above, according to the present embodiment, the timing of obtaining an offset image used for the offset correction of a radiation image is changed, in accordance with the change over time of offset data. That is, when the change over time of offset data is large in still image imaging with the radiation imaging apparatus, the apparatus performs the following operations with a first offset image obtaining timing:
  offset images are periodically obtained in order to determine the stability of the offset images,
  when the setting of imaging conditions is performed, the above-described offset image obtaining is stopped, and
  the offset image used in offset correction immediately after radiation imaging is obtained.

On the other hand, if the change over time of offset data becomes smaller, the apparatus performs the following operations with a second offset image obtaining timing:
  periodic obtaining of offset data is stopped,
  when the setting of imaging conditions is performed, the obtaining of offset data prior to radiation image obtaining is performed, and
  the offset correction of a radiation image is performed using this offset data.

Therefore, even if the change over time of the offset images is large, it is possible to accurately perform the offset correction of an image of an object to be imaged, and when the change over time of the offset images is small, it is possible to shorten the time from a radiation exposure to an image display. Also, in the above-described present embodiment, regardless of the result of the determination of whether offset images are stable, the offset image obtained by the offset image obtaining processing performed following X-ray imaging obtaining processing is used for the generation of a diagnostic image. However, the present invention is not limited to this. If offset images are very stable, the offset image obtained before an X-ray exposure may be used also during the generation of a diagnostic image.

According to the present invention, there is provided a radiation imaging apparatus in which, while the accuracy of offset correction is maintained, it is possible to shorten the time from a radiation exposure to an image display.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-049607, filed Mar. 7, 2011, which is hereby incorporated by reference herein in its entirety.

What is claimed is:

1. An X-ray imaging apparatus comprising:
a sensor array configured to obtain X-ray image data;
a read-out circuit configured to read out electric signals from the sensor array to obtain X-ray image data;
a determination unit configured to determine stability of offset data included in the X-ray image data obtained by the read-out circuit before the X-ray image data is obtained based on data that the read-out circuit has repeatedly read out during a period in which a condition where no X-ray is irradiated continues before an irradiation of the X-ray; and
a control unit configured to, when it is determined that the offset date is stable, perform a first control in which offset data for offset correction to X-ray image data is obtained using the read-out circuit before obtaining the X-ray image data, and perform a second control after the first control, in which X-ray image data is obtained using the read-out circuit.

2. The apparatus according to claim 1, further comprising a correction unit configured to correct X-ray image data obtained by the read-out circuit based on offset data for offset correction obtained by the first control.

3. The apparatus according to claim 1, wherein the control unit prohibits the first control from being performed in a case where the determination unit determines that offset data is not stable.

4. The apparatus according to claim 1, wherein the control unit performs the first control in accordance with an operation input in a case where the determination unit determines that the offset data is stable.

5. The apparatus according to claim 1, further comprising a setting unit configured to set an imaging condition for X-ray image data in accordance with an operation input, wherein the control unit performs the first control in accordance with the operation input in a case where the determination unit determines that offset data is stable.

6. The apparatus according to claim 1, wherein said determination unit determines the stability in each group consisting of a plurality of offset data obtained by repeatedly reading electric signals from the sensor array using the read-out circuit.

7. The apparatus according to claim 6, wherein the determination unit determines the stability based on change of offset data obtained by repeatedly reading electric signals from the sensor array using the read-out circuit.

8. The apparatus according to claim 1, wherein
X-ray image data is obtained by reading electric signals from the sensor array while the sensor array is being irradiated with X-rays, and
offset image data is obtained by reading electric signals from the sensor array while the sensor array is not being irradiated with X-rays.

9. The apparatus according to claim 1, wherein the control unit performs, in a case where the determination unit determines that offset data is not stable, a third control in which offset data for correcting X-ray image data is read by the read-out circuit after the X-ray image data is obtained.

10. The apparatus according to claim 1, wherein the control unit performs, after the second control, a third control in which other offset data for correcting X-ray image data is read by the read-out circuit after the X-ray image data is obtained by the read-out circuit.

11. The apparatus according to claim 10, further comprising a correcting unit configured to correct a first X-ray image based on the X-ray image data using offset data obtained by the first control, and to correct a second X-ray image based on the X-ray image data using the other offset data obtained by the third control.

12. The apparatus according to claim 1, further comprising:
a correction unit configured to correct X-ray image data obtained by the read-out circuit, based on offset data obtained by the first control; and
a display control unit configured to display on a display unit X-ray image data corrected by said correction unit.

13. A control apparatus for controlling X-ray imaging using a sensor array configured to obtain X-ray image data, a driving circuit configured to drive the sensor array, and a read-out circuit configured to read electric signals from the sensor array to obtain X-ray image data, the control apparatus comprising:
a determination unit configured to determine stability of offset data included in the X-ray image data obtained by the read-out circuit before the X-ray image data is obtained based on data that the read-out circuit has repeatedly read out during a period in which a condition where no X-ray is irradiated continues before an irradiation of the X-ray; and
a control unit configured to, when it is determined that the offset date is stable, perform a first control in which offset data for offset correction to X-ray image data is obtained using the read-out circuit before obtaining the X-ray image data, and perform a second control after the first control, in which X-ray image data is obtained using the read-out circuit.

14. A control method of controlling X-ray imaging using a sensor array configured to obtain X-ray image data, a driving circuit configured to drive the sensor array, and a read-out circuit configured to read electric signals from the sensor array to obtain X-ray image data, the method comprising:
determining stability of offset data included in the X-ray image data obtained by the read-out circuit before the X-ray image data is obtained based on data that the read-out circuit has repeatedly read out during a period in which a condition where no X-ray is irradiated continues before an irradiation of the X-ray; and performing, when it is determined that the offset date is stable, a first control in which offset data for offset correction to X-ray image data is obtained using the read-out circuit before obtaining the X-ray image data, and performing a second control after the first control, in which X-ray image data is obtained using the read-out circuit.

15. A non-transitory computer readable storage medium storing a computer program including instructions for causing an apparatus which comprises at least one CPU to execute a control method of controlling X-ray imaging using a sensor array configured to obtain X-ray image data, a driving circuit configured to drive the sensor array, and a read-out circuit configured to read electric signals from the sensor array to obtain X-ray image data, the method comprising:

determining stability of offset data included in the X-ray image data obtained by the read-out circuit before the X-ray image data is obtained based on data that the read-out circuit has repeatedly read out during a period in which a condition where no X-ray is irradiated continues before an irradiation of the X-ray; and performing, when it is determined that the offset date is stable, a first control in which offset data for offset correction to X-ray image data is obtained using the read-out circuit before obtaining the X-ray image data, and performing a second control after the first control, in which X-ray image data is obtained using the read-out circuit.

16. An X-ray imaging apparatus comprising:
a sensor array for obtaining an X-ray image based on irradiated X-ray radiation;
an offset data obtaining unit configured to obtain offset data which are obtained from the sensor array during a period in which a condition where no X-ray radiation is irradiated continues before an irradiation of the X-ray radiation;
a first offset correction unit configured to perform an offset correction on a preview image based on offset data obtained before the sensor array obtains an X-ray image; and
a second offset correction unit configured to perform an offset correction on a preview image and an X-ray image based on offset data obtained after obtaining that X-ray image.

17. The apparatus according to claim 16, wherein an X-ray image on which an offset correction is performed by the second offset correction unit is output to a display unit after a preview image on which an offset correction is performed by the first offset correction unit or a preview image on which an offset correction is performed by the second offset correction unit is output to the display unit.

18. An X-ray imaging apparatus which performs a radiographic image obtaining processing for obtaining an X-ray image by reading an image from a sensor with X-ray irradiation, and an offset image obtaining processing for obtaining an offset image by reading an image form the sensor without X-ray irradiation, the apparatus comprising:
a determination unit configured to determine, based on a predetermined reference, whether or not an offset image obtained by the offset image obtaining processing is stable against time;
an executing unit configured to execute the radiographic image obtaining processing in response to an exposure instruction to obtain an X-ray image;
a display unit configured to perform an offset correction on an X-ray image obtained by the execution unit and display that X-ray image; and
a generating unit configured to generate a diagnostic image from the X-ray image obtained by the execution unit,
wherein the display unit, in a case where it is determined not to be stable by the determination unit, performs the offset correction by using an offset image obtained by executing the offset image obtaining processing following acquisition of the X-ray image by the execution unit, and in a case where it is determined to be stable by the determining unit, the display unit performs the offset correction by using an offset image obtained prior to the acquisition of the X-ray image by the execution unit, and
wherein the generating unit, regardless of a determination result obtained by the determining unit, performs the offset correction on the X-ray image obtained by the execution unit by using an offset image obtained by executing the offset image obtaining processing following acquisition of the X-ray image by the execution unit.

19. The apparatus according to claim 18, wherein the display unit, after it is determined to be stable by the determining unit, performs the offset image obtaining processing in response to input of a setting instruction of an imaging condition to be input prior to the exposure instruction, and performs the offset correction on an X-ray image obtained by the executing unit using an offset image obtained in accordance with the exposure instruction.

20. The apparatus according to claim 19, wherein, after an offset image is determined to have stabilized, in a case where the exposure instructions are repeated a plurality of times after one of the setting instructions is issued, the display unit uses one offset image, which has been obtained in response to the one of the set instructions, for the offset correction on the plurality of radiographic images obtained in response to the exposure instruction repeated the plurality of times.

* * * * *